(12) United States Patent
Krause et al.

(10) Patent No.: US 11,355,246 B2
(45) Date of Patent: *Jun. 7, 2022

(54) IDENTIFYING AND RANKING RISK FACTORS USING TRAINED PREDICTIVE MODELS

(71) Applicant: International Business Machines Corporation, Armonk, NY (US)

(72) Inventors: Josua Krause, New York, NY (US); Kenney Ng, Arlington, MA (US); Adam Perer, Pittsburgh, PA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1236 days.

This patent is subject to a terminal disclaimer.

(21) Appl. No.: 15/172,512

(22) Filed: Jun. 3, 2016

(65) Prior Publication Data

US 2017/0323063 A1 Nov. 9, 2017

Related U.S. Application Data

(63) Continuation of application No. 15/144,948, filed on May 3, 2016.

(51) Int. Cl.
*G16H 50/30* (2018.01)
*G06N 20/00* (2019.01)
(Continued)

(52) U.S. Cl.
CPC ............ *G16H 50/30* (2018.01); *G06N 20/00* (2019.01); *G16H 10/60* (2018.01); *G16H 50/20* (2018.01)

(58) Field of Classification Search
CPC ..... G16H 50/20; G16H 50/30; G01N 2800/50
See application file for complete search history.

(56) References Cited

U.S. PATENT DOCUMENTS 7,805,388 B2 9/2010 Weston et al.
8,108,324 B2 1/2012 Krupka et al.
(Continued)

OTHER PUBLICATIONS

Anonymous "A Method for Clinical Risk Prediction across Heterogeneous Feature Types using Multi-linear Regression Models"; ip.com; IP.com No. IPCOM000238067d; Jul. 30, 2014; 5 pages.
(Continued)

*Primary Examiner* — Reginald R Reyes
(74) *Attorney, Agent, or Firm* — Cantor Colburn LLP; Kristofer Haggerty

(57) ABSTRACT

Embodiments are directed to methodologies, systems and computer program products for generating, for each of a plurality of risk factors in a patient database containing information of a plurality of patients, an index of input values for the risk factor. For each patient P of the plurality of patients, a series of local impact scores is computed for the patient. Computing the series of local impact scores for the patient includes calculating a risk score for the patient with respect to each of the indexed input values for each of the plurality of risk factors. For at least one of the plurality of patients, at least some of the plurality of risk factors are ranked based at least partly on the computed local impact scores for each of the at least some risk factors, and an indication of the ranked risk factors for the at least one patient is provided.

5 Claims, 4 Drawing Sheets

(51) Int. Cl.
   *G16H 50/20*      (2018.01)
   *G16H 10/60*      (2018.01)

(56) References Cited

U.S. PATENT DOCUMENTS

| | | | |
|---|---|---|---|
| 8,694,300 | B2 | 4/2014 | Morris et al. |
| 2003/0212579 | A1* | 11/2003 | Brown .................. A61B 5/411 600/300 |
| 2010/0088264 | A1 | 4/2010 | Teverovskiy et al. |
| 2010/0191685 | A1 | 7/2010 | Sapir et al. |
| 2014/0095184 | A1 | 4/2014 | Gotz et al. |
| 2014/0303988 | A1* | 10/2014 | Maneri .................. G16H 15/00 705/2 |
| 2014/0377777 | A1* | 12/2014 | Anderberg ......... G01N 33/6893 435/7.94 |
| 2015/0157685 | A1* | 6/2015 | Wilson ................ A61K 31/404 424/179.1 |
| 2017/0323075 | A1 | 11/2017 | Krause et al. |
| 2017/0340293 | A1* | 11/2017 | Al-Ali .................... A61B 5/743 |

OTHER PUBLICATIONS

Dong et al. "Evaluation of a risk factor scoring model in screening for Undiagnosed diabetes in China population"; Journal of Zhejiang University—Science B (Biomedicine & Biotechnology); Jul. 27, 2011; 7 pages.

Elzen, et al.; "Interactive Construction and Analysis of Decision Trees"; Eindhoven University of Technology; IEEE Symposium on Visual Analytics Science and Technology; Oct. 2011; 10 pages.

Friedman, Jerome H.; Greedy Function Approximation: A Gradient Boosting Machine1; The Annals of Statistics 2001, vol. 29, No. 5, 1189-1232; Apr. 2001; 44 pages.

IBM "List of IBM Patents or Patent Applications treated as Related", Date Filed: Oct. 24, 2019, p. 1-2.

Martins, et al.; "Signal Propagation in Bayesian Networks and its Relationship with Intrinsically Multivariate Predictive Variables"; Informational Sciences; Oct. 2012; 3 pages.

Olden, et al.; "Illuminating the "black box": a randomization approach for understanding variable contributions in artificial neural networks"; Ecological Modelling; May 2000; 16 pages.

* cited by examiner

IDENTIFYING AND RANKING RISK FACTORS USING TRAINED PREDICTIVE MODELS

DOMESTIC PRIORITY

This application is a continuation of U.S. patent application Ser. No. 15/144,948, filed May 3, 2016, the disclosure of which is incorporated by reference herein in its entirety.

BACKGROUND

This disclosure relates to identifying patient-specific risk factors and, more specifically, to identifying and ranking risk factors in accordance with patient-specific importance using trained predictive models.

Individual patients may be associated with a wide variety of quantifiable factors related to various conditions, each of which may be associated directly or indirectly with risks of developing or exacerbating such conditions. Each such risk factor, when examined across a large population, may be associated with a wide range of values. For example, a risk factor such as blood cholesterol levels may comprise a large number of individual values when examined across a similarly large number of individual patients, and may be linked to any number of conditions (e.g., obesity, diabetes, etc.).

Predictive modeling has been applied to a number of use cases including the early detection of disease onset and the greater individualization of care. In general, a predictive model is a function that maps an instance to a target label with an associated score. The true relationship between instances and the corresponding labels is typically unknown or hard to describe by an explicit rule. Trained predictive models are typically trained using labeled training data for a specific condition, and are typically intended to identify relationships between a particular risk factor and one or more patients' chances of developing or exacerbating that specific condition ("predictive risk"). However, existing solutions that utilize such trained predictive models do not take into account how new or changing risk factor values may lead to changes in predictive risk.

SUMMARY

According to at least one embodiment, a computer-implemented method is provided. The method is implemented by one or more computing systems configured to identify impactful patient-specific risk factors and includes generating, for each of a plurality of risk factors in a patient database containing information of a plurality of patients, an index of input values for the risk factor by determining all values for the risk factor that are associated with the plurality of patients. The method further includes computing, for each patient P of the plurality of patients, a series of local impact scores for the patient. Computing the series of local impact scores for the patient includes, for each risk factor R in the plurality of risk factors and for each input value V in the generated index for the risk factor R, creating a new patient model NP such that the input value V for risk factor R is assigned to the new patient model NP and, for each of all other risk factors associated with patient P, assigning to the new patient model NP the value associated with patient P for the risk factor. Computing the series of local impact scores for the patient further includes determining, using a trained predictive model and based on each of the created new patient models, a local impact score S for the risk factor R. The method further includes, for at least one of the plurality of patients, ranking at least some of the plurality of risk factors based at least in part on the computed local impact scores for each of the at least some risk factors, and providing an indication of the ranked at least some risk factors for the at least one patient.

According to at least one embodiment, a computer-implemented method is provided. The method is implemented by one or more computing systems configured to identify impactful patient-specific risk factors and includes generating, for each of a plurality of risk factors in a patient database containing information regarding a plurality of patients, an index of input values for the risk factor. For each patient P of the plurality of patients, a series of local impact scores is computed for the patient. Computing the series of local impact scores for the patient includes calculating a risk score for the patient with respect to each of the indexed input values for each of the plurality of risk factors. For at least one of the plurality of patients, at least some of the plurality of risk factors are ranked based at least in part on the computed local impact scores for each of the at least some risk factors, and an indication of the ranked risk factors for the at least one patient is provided.

According to another embodiment, a non-transitory computer-readable storage medium has computer-readable program code stored thereon that, when executed, causes one or more computing systems to identify impactful patient-specific risk factors by performing a method. The method includes generating, for each of a plurality of risk factors in a patient database containing information regarding a plurality of patients, an index of input values for the risk factor. For each patient P of the plurality of patients, a series of local impact scores is computed for the patient. Computing the series of local impact scores for the patient includes calculating a risk score for the patient with respect to each of the indexed input values for each of the plurality of risk factors. For at least one of the plurality of patients, at least some of the plurality of risk factors are ranked based at least in part on the computed local impact scores for each of the at least some risk factors, and an indication of the ranked risk factors for the at least one patient is provided.

According to another embodiment, a system comprises one or more processors, a system memory, and a bus that couples various system components including the system memory to the one or more processors. The system is configured to identify impactful patient-specific risk factors by performing a method that includes generating, for each of a plurality of risk factors in a patient database containing information regarding a plurality of patients, an index of input values for the risk factor by determining all values for the risk factor that are associated with the plurality of patients. For each patient of the plurality of patients, a series of local impact scores for the patient is computed by at least, for each risk factor in the plurality of risk factors creating a new patient model for each respective input value in the generated index for the risk factor. The respective input value is assigned to the new patient model for the risk factor and, for each of all other risk factors associated with the patient, the value associated with the patient for the other risk factor is assigned to the new patient model. Using a trained predictive model and based on each of the created new patient models, a local impact score is determined for the risk factor and, for at least one of the plurality of patients, at least some of the plurality of risk factors are ranked based at least partly on the computed local impact scores for each of the at least some risk factors. An indication of the ranked risk factors for the at least one patient is provided.

According to another embodiment, a system comprises one or more processors, a system memory, and a bus that couples various system components including the system memory to the one or more processors. The system is configured to identify impactful patient-specific risk factors by performing a method that includes generating, for each of a plurality of risk factors in a patient database containing information regarding a plurality of patients, an index of input values for the risk factor. For each patient P of the plurality of patients, a series of local impact scores is computed for the patient. Computing the series of local impact scores for the patient includes calculating a risk score for the patient with respect to each of the indexed input values for each of the plurality of risk factors. For at least one of the plurality of patients, at least some of the plurality of risk factors are ranked based at least in part on the computed local impact scores for each of the at least some risk factors, and an indication of the ranked risk factors for the at least one patient is provided.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

DETAILED DESCRIPTION

One or more embodiments described herein enable one or more processor-based computing systems to automatically identify patient-specific risk factors in trained predictive models, and in particular to rank such patient-specific risk factors in accordance with local importance. In this manner, the described techniques may simplify the exploration of the predicted risk space by enabling identification of one or more small changes in value for particular risk factors that may yield a significantly large change in the predicted risk for a particular condition.

As used herein, the term "risk factor" refers to any feature associated with finite possibilities for quantitative or qualitative input values. The term "patient," also as used herein, may refer to any individual collection of risk factors, while "patient database" may refer to any body of stored data that relates to multiple such patients. One typical but non-exclusive example of a "patient" as used herein is a human medical subject associated with a vector (or list) of risk factors such as height, weight, gender, cholesterol level, body mass index (BMI), age, etc. For each patient, a vector of risk factors derived from patient health data such as electronic medical records (e.g., diagnoses, lab results, medications, procedures, hospitalization records); questionnaire data; genetic information; activity/diet tracking data; microbiome data; actigraphy data; and other suitable sources.

The term "local impact" refers to an amount of variation in predictive risk associated with a change of input value for a particular risk factor for a particular patient. The term "local importance" refers to the degree of change to the input value for a risk factor needed to result in a corresponding change to the predictive risk for a particular condition for a particular patient.

As used herein, the term "predictive model" refers to any classifier trained on labeled training data for a specific risk target or condition. Generally, the techniques described herein may be used with any predictive model, including those for use outside the realms of clinical healthcare and medical diagnosis, and may in certain embodiments be based at least in part on one or more statistical classification algorithms (e.g., logistic regression, decision trees, random forests, support vector machines, neural networks, and Bayesian networks). Similarly, the term "patient" can be generalized to represent any entity that can be represented as a vector (or list) of features associated with the entity.

Figure 1:
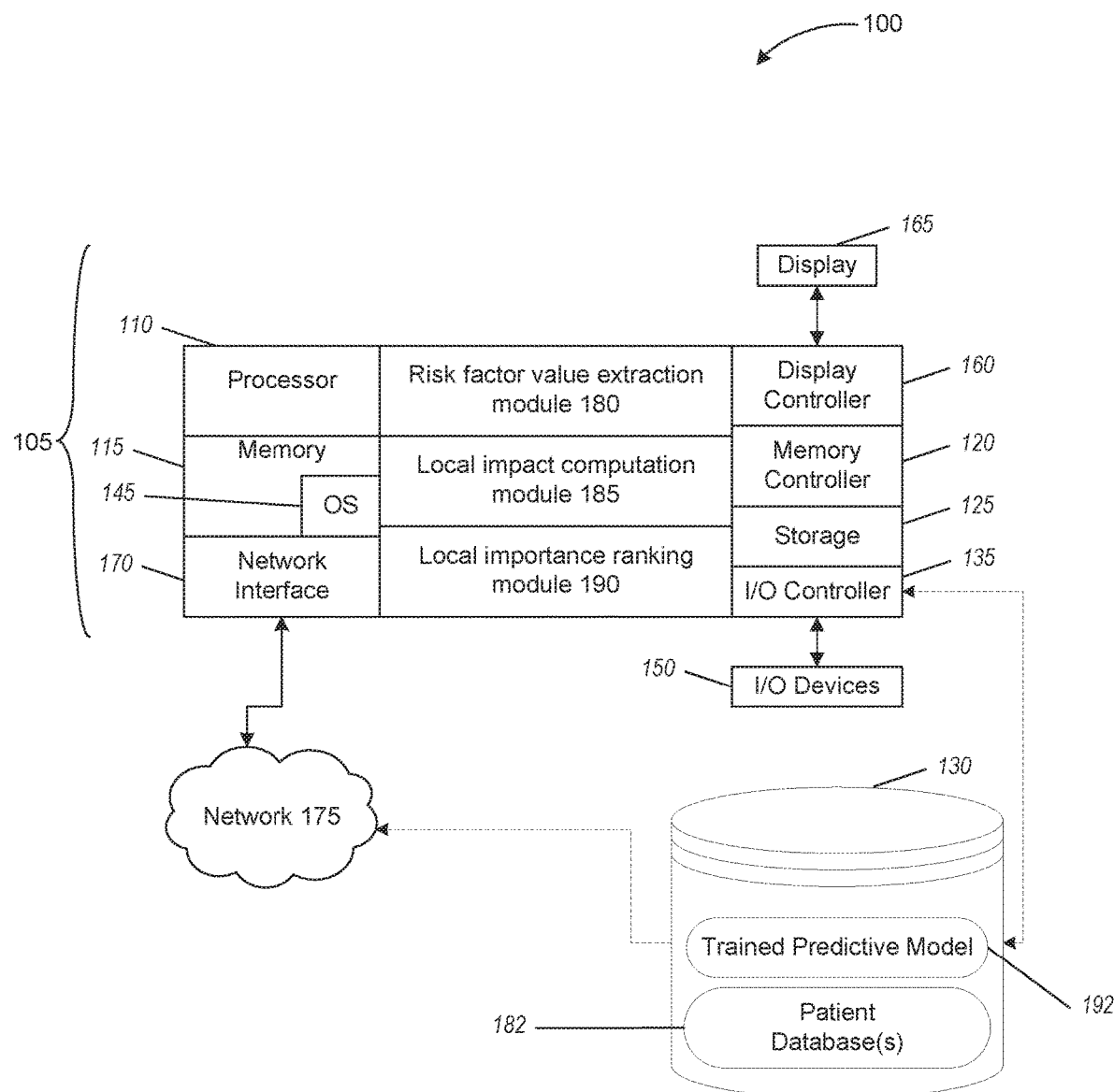
FIG. 1 depicts a block diagram of a risk factor impact assessment system in accordance with an embodiment.

With reference now to FIG. 1, a block diagram of a computing system 100 for use in practicing the teachings herein is depicted. The methods described herein can be performed or otherwise implemented via hardware, software (e.g., firmware), or combination thereof. In an exemplary embodiment, the methods described herein are implemented in hardware, and may be part of the microprocessor of a special or general-purpose digital computer, such as a personal computer, workstation, minicomputer, or mainframe computer. The computing system 100 therefore includes computer 105.

In the illustrated embodiment of FIG. 1, the computer 105 includes a processor 110, a memory 115 coupled to a memory controller 120, internal storage 125, and one or more input and/or output (I/O) devices 150 that are communicatively coupled to the computer 105 via a local input/output controller 135. The input/output controller 135 may include one or more buses or other wired or wireless connections, as is known in the art. The input/output controller 135 may further include additional elements, which are omitted for simplicity, such as controllers, buffers (caches), drivers, repeaters, and receivers, to facilitate communications. Further, the local interface may include address, control, and/or data connections to facilitate appropriate communications among the aforementioned components. In the depicted embodiment, the computing system 100 further includes a display controller 160 coupled to a display 165, and a network interface 170 communicatively coupled to a network 175. The computing system 100 is communicatively coupled to external storage 130 via one or both of the local input/output controller 135 and the network interface 170.

Also in the illustrated embodiment, the processor 110 is a hardware device for executing hardware instructions or software, particularly that stored in memory 115. The processor 110 can be any custom made or commercially available processor, a central processing unit (CPU), an auxiliary processor among several processors associated with the general-purpose computer 105, a semiconductor based microprocessor (in the form of a microchip or chip set), a macroprocessor, or generally any device for executing instructions.

The memory 115 can include any one or combination of volatile memory elements (e.g., random access memory (RAM, such as DRAM, SRAM, SDRAM, etc.)) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 115 may incorporate electronic, magnetic, optical, and/or other types of storage media. Note that the memory 115 can have a distributed architecture, where various components are situated remote from one another, but can be accessed by the processor 110.

The instructions in the memory 115 may include one or more separate programs, each of which comprises an ordered listing of executable instructions for implementing logical functions. In the example of FIG. 1, the instructions in the memory 115 include a suitable operating system (OS) 145. The operating system 145 typically controls the execution of other computer programs and may, among other capabilities, provide scheduling, input-output control, file and data management, memory management, and communication control and related services.

In an exemplary embodiment, I/O devices 150 may include, as non-limiting examples, a keyboard, mouse, printer, scanner, microphone, a network interface card (NIC) or modulator/demodulator (for accessing other files, devices, systems, or a network), a radio frequency (RF) or other transceiver, a telephonic interface, a bridge, a router, and other peripherals communicatively coupled to the computer 105 via input/output controller 135.

The network 175 may be an IP-based network for communication between computer 105 and any external server, client and the like via a broadband or other network connection. The network 175 transmits and receives data between the computer 105 and external systems. In an exemplary embodiment, the network 175 may be a managed IP network administered by a service provider. The network 175 may be implemented in a wireless fashion, e.g., using wireless protocols and technologies, such as WiFi, WiMax, etc. The network 175 may also be a packet-switched network such as a local area network, wide area network, metropolitan area network, Internet network, or other similar type of network environment. The network 175 may be a fixed wireless network, a wireless local area network (LAN), a wireless wide area network (WAN) a personal area network (PAN), a virtual private network (VPN), intranet or other suitable network system and includes equipment for receiving and transmitting signals.

In at least some embodiments, the memory 115 may further include a basic input output system (BIOS) (omitted for simplicity). The BIOS is a set of routines that initialize and test hardware at startup, initiate execution of the OS 145, and support the transfer of data among the hardware devices. The BIOS is typically stored in ROM so that the BIOS may be executed when the computer 105 is activated. When the computer 105 is in operation, the processor 110 is configured to execute instructions stored within the memory 115, to communicate data to and from the memory 115, and to generally control operations of the computer 105 pursuant to the instructions.

Also in the illustrated embodiment, the computer 105 further includes a risk factor value extraction module 180, such as may be used to process one or more patient databases 182; local impact computation module 185; and local importance ranking module 190. While in the illustrated embodiment the patient databases 182 and trained predictive model 192 reside in the same external storage 130, in various scenarios and embodiments such patient databases and trained predictive models may be provided to the computer 105 (and modules thereof) in other suitable matters. For example, the trained predictive models may reside in separate external storage from the patient databases, may be provided via the network 175 and network interface 170 while patient databases are provided locally via I/O controller 135, etc.

Figure 2:
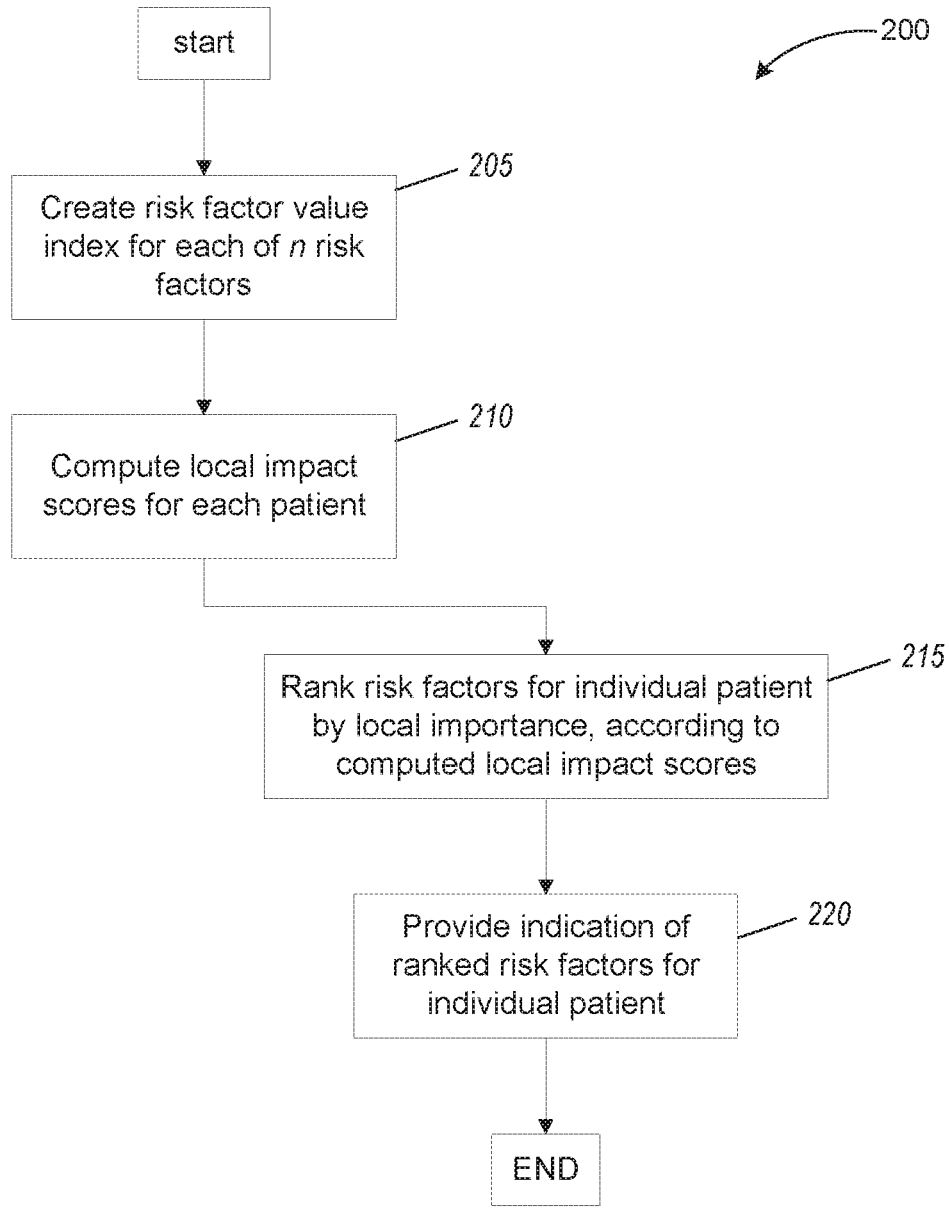
FIG. 2 depicts a process flow of a risk factor impact assessment system in accordance with an embodiment.

FIG. 2 depicts a methodology or routine 200 for a risk factor impact assessment, such as may be performed to assess and rank the importance of patient-specific risk factors using trained predictive models (and such as might, in certain embodiments, be performed by the computer 105 of FIG. 1).

Figure 3:
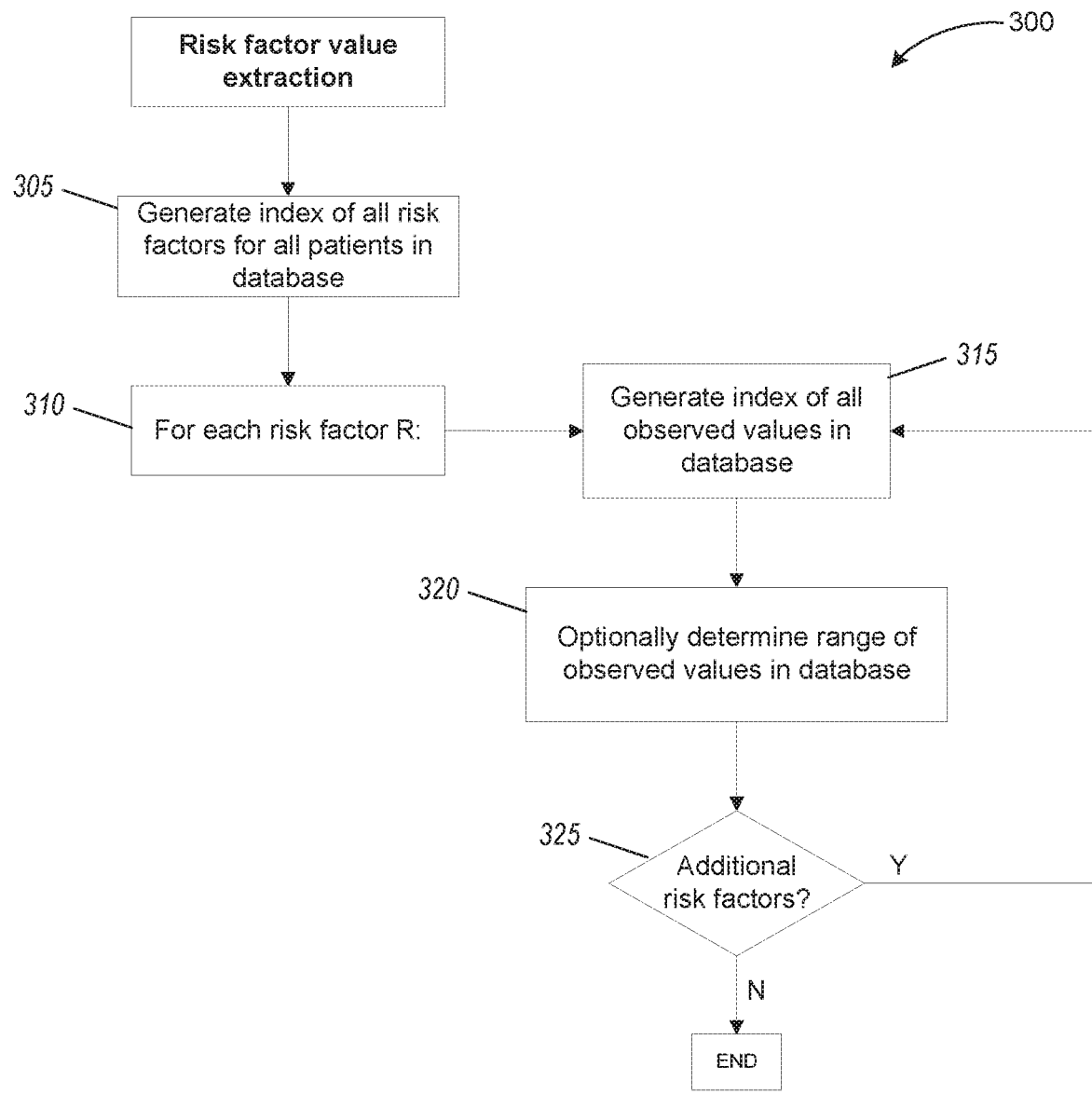
FIG. 3 depicts a process flow of a risk factor value extraction routine in accordance with an embodiment.

The routine 200 begins at block 205, in which a processor-based device assesses all patients in a patient database (not shown) in order to generate a risk factor value index for each of n risk factors occurring in the patient database. FIG. 3 depicts an embodiment of the creation of such a risk factor value index in more detail. The resulting risk factor value index includes all possible inputs for every risk factor in the patient database. As one non-exclusive benefit, computations may thereby be optimized to utilize only realistic data inputs.

In certain embodiments, an alternative approach may be utilized with respect to some or all of the risk factors, such that a range of observed values in the patient database is determined. For example, assume that a risk factor of "LDL-cholesterol" is associated with multiple patients in the database, and that the individual input values for those patients' LDL-cholesterol levels occur with an approximately Gaussian distribution between 80 mg/dL and 450 mg/dL. In certain embodiments, the index for the "LDL-cholesterol" risk factor may be generated to specify a continuous range from 80-450 mg/dL, even if no patient is observed in the database with the particular value of 96.7 mg/dL. In this manner, the index may provide the basis for determining predictive risk variations for every possible value in the specified range (including 96.7 mg/dL), rather than limiting such predictive risk variations to the particular values associated with patients in the database.

The routine 200 continues at block 210, in which the processor-based device computes local impact scores for each of at least some patients in the patient database. The computation of the local impact scores is depicted with greater detail in FIG. 4. In at least some embodiments, computing the local impact scores includes, for each patient in a patient database, creating a set of new patient models for the patient for each input value possible for each risk factor in the patient database.

For example, given a simplistic patient database that includes a quantity p patients that encompass a quantity of r risk factors such that v input values are possible for each individual risk factor, computing the local impact scores may include creating a set of p×r×v new patient models. In practice, such a scenario is unlikely, as each risk factor in a given patient database is generally associated with a distinct quantity of possible input values (rather than all risk factors being associated with an identical quantity of possible input values). As part of generating a new patient model, a single risk factor is assigned a new value corresponding to one of the plurality of other possible input values for that risk factor, while all other risk factors are assigned values corresponding to those associated with the particular "real" patient.

Thus, for each particular patient, an array of distinct patient models is created for each input value for every risk factor extracted from the patient database, with each created patient model being differentiated from the original "real" patient by only a single input value for each risk factor. For each new patient model created, a local impact score (alternatively termed a "risk score") is calculated. In at least certain embodiments, the local impact score may be calculated by providing a trained predictive model with inputs corresponding to the new patient model, such that the trained predictive model provides a quantifiable risk score associated with the new patient model.

As a result of computing the local impact scores, it is possible to identify how each patient's predictive risk score will respond to every possible observed value for every risk factor.

The routine 200 continues at block 215, in which the processor-based device ranks risk factors for individual patients in the patient database according to local importance based at least in part on the computed local impact scores from block 210. In order to rank risk factors in this manner, local importance for each risk factor is determined as the smallest change in value needed to have the largest change in predicted risk. Local importance can therefore be used to re-rank risk factors for a specified patient, as well as to determine suggestions for increasing or decreasing predicted risk for that patient.

Localized importance of risk factors is computed by examining the range of possible predicted risk scores a risk factor can result in, starting from each patient's actual risk factor value. Values close to the original value are weighted higher than those further away. Then, compute impactful changes, which are the smallest change needed to have the largest change in the predicted outcome. In at least some embodiments, therefore, local importance is determined in order to maximize the quantity:

$$\mathrm{argmax}_x \frac{|pred_f(x) - pred_f(x_f)|}{\sigma_f \sqrt{2\pi}} e^{-\frac{(x-x_f)^2}{2\sigma_f^2}}$$

where $|pred_f(x)-pred_f(x_f)|$ is the difference in magnitude between the predicted risk score for a particular risk factor associated with the "real" patient and the predicted risk score associated with that risk factor for the new patient model, $(x-x_f)^2$ is the amount of change in the risk factor value from the "real" patient model to the new patient model, and $\sigma_f^2$ is the observed standard deviation of the risk factor values in the patient database. In other embodiments, local importance may be calculated by determining the smallest change in value for the risk factor needed to result in a change of a predetermined magnitude to the predicted risk. In another embodiment, local importance can be determined by maximizing the above quantity using a signed difference in magnitude between the predicted risk score associated with the "real" patient ($pred_f(x)$) and the predicted risk score associated with the new patient model ($pred_f(x_f)$) instead of its absolute value. In this embodiment $pred_f(x)-pred_f(x_f)$ would be used for impacts towards a decrease in the predicted risk score and $-(pred_f(x)-pred_f(x_f))$ would be used for impacts towards an increase in the predicted risk score.

Returning to FIG. 2, the routine 200 continues at block 220, in which the processor-based device provides one or more indications of ranked risk factors related to a particular condition for an individual patient. In certain embodiments, such indications may include suggested values for one or more risk factors in order to alter the predicted risk associated with that patient.

FIG. 3 depicts a process flow of a risk factor value extraction routine 300 (such as may be performed by the risk factor value extraction module 180 of FIG. 1) in accordance with an embodiment.

The routine 300 begins at block 305, in which a processor-based device generates a data-driven index of all risk factors occurring by scanning all patient records in a patient database. At block 310, the routine 300 begins processing each risk factor R within the generated index.

For each risk factor R, the routine 300 at block 315 generates an index of all observed values for the risk factor R occurring in the patient database. At block 320, the routine 300 optionally determines a range of observed values in the patient database.

At block 325, the routine 300 determines whether additional indexed risk factors need to be processed. If so, the routine 300 proceeds to block 315 to generate an additional index related to values for the next risk factor R; if not, the routine 300 ends.

Figure 4:
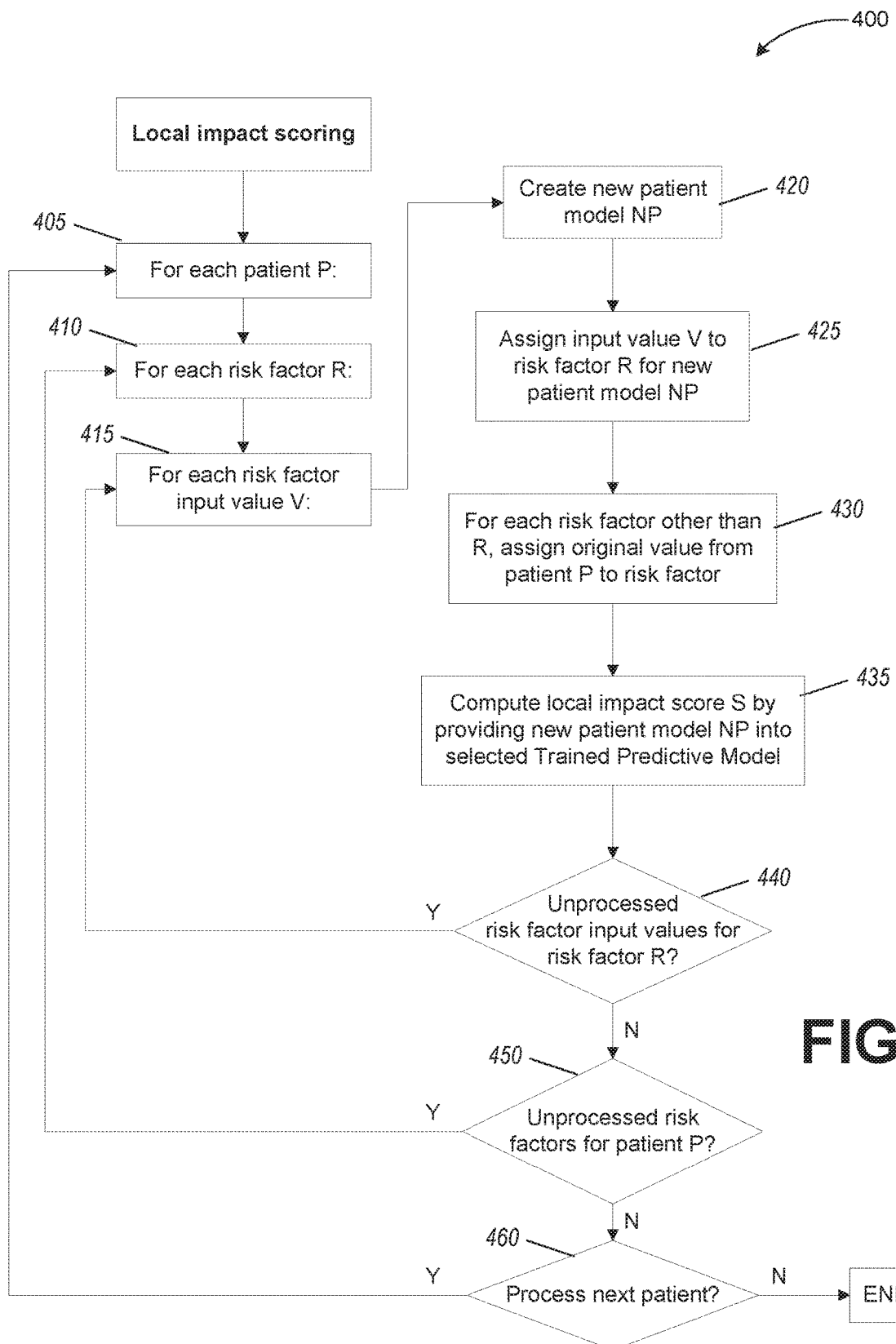
FIG. 4 depicts a process flow of a local impact scoring routine in accordance with an embodiment.

FIG. 4 depicts a process flow of a local impact scoring routine 400 (such as might be performed by the local impact computation module 185 of FIG. 1) in accordance with an embodiment.

The routine 400 begins at block 405, in which a processor-based device begins to process database records associated with a first patient P. As part of processing patient P, in block 410 the processor-based device begins to process a first risk factor R (e.g., of a plurality of risk factors indexed based on patient data from the selected database) for patient P. As part of processing risk factor R, in block 415 the processor-based device begins to process each indexed risk factor input value V for risk factor R.

In block 420, the routine 400 creates a new patient model NP based on the actual patient P. In block 425, the routine 400 assigns the input value V to risk factor R for the new patient model; and in block 430, the routine 400 assigns the original values from patient P for all risk factors other than the current risk factor R. In block 435, the routine 400 computes a local impact score S to be associated with the new patient model NP by providing that patient model into a trained predictive model.

In block 440, the routine 400 determines whether there are remaining unprocessed risk factor input values for risk factor R. If so, the routine 400 returns to block 415 in order to process the next indexed input value for risk factor R; if not, the routine 400 proceeds to block 450.

Thus, as noted above for each particular patient an array of distinct patient models is created such that each created patient model NP is differentiated from the original patient P by only a single input value V for each risk factor R.

In block 450, as all indexed input values for risk factor R have been processed, the routine 400 determines whether there are remaining unprocessed risk factors for patient P. If so, the routine 400 returns to block 410 in order to process the next indexed risk factor; if not, the routine 400 proceeds to block 460.

In block 460, as all risk factors for patient P have been processed, the routine 400 determines whether to process a next patient. If it is determined to process a next patient, the routine 400 returns to block 405. If it is determined not to process a next patient (such as if an explicit instruction to perform local impact scoring for only a single patient or a subset of patients has been received), the routine 400 ends.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It will be appreciated that in some embodiments the functionality provided by the methodologies or routines discussed above may be provided in alternative ways, such as being split among more routines or consolidated into fewer routines. Similarly, in some embodiments illustrated routines may provide more or less functionality than is described, such as when other illustrated routines instead lack or include such functionality respectively, or when the amount of functionality that is provided is altered. In addition, while various operations may be illustrated as being performed in a particular manner (e.g., in serial or in parallel) and/or in a particular order, it will be appreciated that in other embodiments the operations may be performed in other orders and in other manners. It will also be appreciated that particular data structures discussed above may be structured in different manners, such as by having a single data structure split into multiple data structures or by having multiple data structures consolidated into a single data structure. Similarly, in some embodiments, illustrated data structures may store more or less information than is described, such as when other illustrated data structures instead lack or include such information respectively, or when the amount or types of information that is stored is altered.

The present invention may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A system comprising one or more processors, a system memory, and a bus that couples various system components including the system memory to the one or more processors, the system configured to identify impactful patient-specific risk factors by performing a method that includes:
   for each of a plurality of risk factors in a patient database containing information of a plurality of patients, generating, via neural network, an index of input values for the risk factor, wherein at least one risk factor of the plurality of risk factors includes LDL-cholesterol, and wherein a range of the index of input values spans from a lowest observed value to a highest observed value in the patient database;
   for each patient P of the plurality of patients, computing, by a trained predictive model of the neural network, a series of local impact scores for the patient, wherein computing the series of local impact scores for the patient includes calculating a risk score for the patient with respect to each of the indexed input values for each of the plurality of risk factors, wherein computing the series of local impact scores for each patient P includes, for each risk factor R in the plurality of risk factors:
   creating, for each input value V in the generated index for the risk factor R, a new patient model NP; and
   determining, using the trained predictive model and based on each of the created new patient models, a local impact score S for the risk factor R; and
   for at least one of the plurality of patients, ranking, by the trained predictive model of the neural network, at least some of the plurality of risk factors based at least in part on the computed local impact scores for each of the at least some risk factors, and providing an indication of the ranked at least some risk factors for the at least one patient, wherein computing the local impact scores comprises:
   examining a range of possible predicted scores for each risk factor of the plurality of risk factors for each patient P, wherein each range begins with each patient P's actual risk score, and
   weighting each patient P's predictive risk score based on a proximity to each patient P's respective actual risk score
   outputting the series of local impact scores.

2. The system of claim 1, wherein generating the index of input values for a risk factor includes determining all values for the risk factor that are associated with the plurality of patients.

3. The system of claim 1, wherein computing the series of local impact scores for each patient P includes, for each risk factor R in the plurality of risk factors:
   creating, for each input value V in the generated index for the risk factor R, a new patient model NP; and
   determining, using the trained predictive model and based on each of the created new patient models, a local impact score S for the risk factor R.

4. The system of claim 1, wherein computing a series of local impact scores for the patient includes computing the series of local impact scores using the trained predictive model that is based at least in part on one or more of a plurality of statistical classification algorithms that include at least one of logistic regression, decision trees, random forests, support vector machines, neural networks, and Bayesian networks.

5. The system of claim 1, wherein ranking the at least some risk factors based at least in part on the computed local impact score S for each of the at least some risk factors includes determining, for each of the at least some risk factors, a local importance score by calculating a smallest change in value for the risk factor needed to result in a largest change to a predicted risk for the at least one patient.

* * * * *